United States Patent [19]
Agonis et al.

[11] Patent Number: 5,883,692
[45] Date of Patent: Mar. 16, 1999

[54] VISUAL FIELD MEASUREMENT APPARATUS

[75] Inventors: Dale Lawrence Agonis, Hebron, Ind.; Andrew Ki Hyon Kim, Winnetka, Ill.; Morgan Nathaniel Wesley; Newton K. Wesley, both of Northbrook, Ill.

[73] Assignee: Retsan, Inc., Northbrook, Ill.

[21] Appl. No.: 942,172

[22] Filed: Oct. 1, 1997

[51] Int. Cl.⁶ .................................................. A61B 3/024
[52] U.S. Cl. ............................................................ 351/224
[58] Field of Search ...................................... 351/222, 223, 351/224, 225, 226, 239, 243, 246; 345/426, 427

[56] References Cited

U.S. PATENT DOCUMENTS

| | | |
|---|---|---|
| 4,146,311 | 3/1979 | Murr . |
| 4,169,664 | 10/1979 | Bailey, Jr. . |
| 4,180,325 | 12/1979 | Humphrey . |
| 4,334,738 | 6/1982 | Seckinger . |
| 4,334,739 | 6/1982 | Seckinger . |
| 4,421,393 | 12/1983 | Cohen et al. . |
| 4,526,452 | 7/1985 | Hirsch . |
| 4,561,738 | 12/1985 | Humphrey et al. . |
| 4,669,835 | 6/1987 | Humphrey . |
| 4,739,410 | 4/1988 | Lehmer et al. . |
| 4,765,731 | 8/1988 | Williams ................................ 351/243 |
| 5,024,519 | 6/1991 | Howard et al. .......................... 351/226 |
| 5,046,835 | 9/1991 | Billeter et al. . |
| 5,050,983 | 9/1991 | Johnson et al. . |
| 5,108,170 | 4/1992 | Sugiyama . |
| 5,319,398 | 6/1994 | Weijland . |
| 5,323,194 | 6/1994 | Campbell . |
| 5,453,827 | 9/1995 | Lee . |
| 5,461,436 | 10/1995 | Campbell . |
| 5,463,431 | 10/1995 | Suzuki et al. . |
| 5,565,949 | 10/1996 | Kasha, Jr. . |
| 5,581,225 | 12/1996 | Seibang et al. . |
| 5,684,937 | 11/1997 | Oxaal ..................................... 345/427 |

OTHER PUBLICATIONS

Global CONTACTO; National Eye Research Foundation, vol. 35/No. 2, 1992.
Visual Fields by T.A. Brombach.
Perimetry and its Clinical Correlations.
Eyeing Glaucoma in Virtual Reality; Buisness Week, Jun. 30, 1997, p. 92.
He'll Help Others See The Light, Parade Magazine, Apr. 27, 1997, pp. 16 and 17.
Kasha Visual Field System; Kasha Software, Inc. (patent pending) May 1, 1997. Kuf—Brochure.
Make Perimetry Work For You: How To Pick The Best Perimeter For Your Practice; Optometric Management, Apr. 1993, pp. 59–61.

Primary Examiner—George Manuel
Attorney, Agent, or Firm—Wallenstein & Wagner, Ltd.

[57] ABSTRACT

A system is provided for measuring the color visual fields of a patient's eyes, and includes a viewing area for the patient to direct one of their eyes toward. The viewing area also has a viewing area perimeter, and the viewing area is divided into four substantially equal quadrants. The system further includes a fixation structure, which is located substantially at a central portion of the viewing area. Generally, the purpose of the fixation structure is to hold the attention of the patient. There are also a plurality of predetermined and substantially linear paths included in the system. The paths extend in directions radially outward from the fixation structure toward the viewing area perimeter. The plurality of predetermined paths are spaced apart by substantially equal angles of separation. Also, each quadrant of the viewing area includes at least two predetermined paths therein. A stimuli target is also provided to continuously and automatically move along the predetermined paths. The stimuli target moves in a direction beginning at a beginning point on the viewing area and continues toward an ending point for each path. The stimuli target completes movement on a first path before beginning movement on a second path.

21 Claims, 13 Drawing Sheets

VISUAL FIELD MEASUREMENT APPARATUS

DESCRIPTION

TECHNICAL FIELD

The present invention relates generally to the testing of visual fields. More particularly, this invention relates to a computerized visual field perimeter.

BACKGROUND OF THE INVENTION

The visual field of a human eye is the area simultaneously visible to one eye without movement. This area is also known as the peripheral or indirect vision and is the area that surrounds the central or direct vision. More technically, the peripheral vision is that which results from retinal stimulation beyond the macula. Additionally, color perception is closely related to visual acuity for objects. In a similar way that vision decreases as it approaches the perimeter of the visual field, so does the color sense become lessened. As the outer perimeter of the visual field is approached, partial color blindness is followed by a space where the entire color sense is lacking. The variation in this peripheral field, for the several colors, gives rise to perimetry. It is with the measurement of the behavior of these peripheral portions of the retina that this invention is concerned with.

Generally speaking, perimetry takes a visual field by fixating a patient's eye in its central vision while introducing stimuli targets of light in the peripheral vision. By presenting large numbers of light stimuli throughout the visual field and recording the patient's reaction to these stimuli, a mapping of the visual field may be obtained.

It is particularly important to obtain visual field mappings when diagnosing and treating diseases which affect the visual field, such as glaucoma. Currently, most visual field mappings are obtained by machines. These machines are called automated visual field perimeters or computerized perimeters. These machines present light stimuli or targets, monitor the central vision fixation, record the reaction to targets, and map the visual field.

Computerized Perimeters

The majority of automated perimeters are specialized pieces of hardware. Each typically consists of a projection area, an embedded controller, an input device for an operating technician, an input device for the patient, and a method of printing results. These machines are built for physician's offices or hospitals. As a result they are, bulky, not portable, and usually require a separate room. These types of devices are also very expensive. Most automated perimeters cost between $7000 and $23,000.

The process and apparatus used by a typical computerized perimeter are described in U.S. Pat. No. 4,349,250 to Gelius (1982). The process outlined in this patent contains the general steps used by most perimeters. These steps include setting up the patient, pretesting for an individual threshold, modifying the program based on this threshold, monitoring fixation, running the test, and displaying results. The process also contains the useful but not completely necessary step of value comparison with standard values. The apparatus detailed in this patent is very specialized. Consequently, it is expensive to build and maintain, and it is not portable.

Another drawback to most computerized perimeters is the fatiguing nature of the test. In most perimeters, a patient is asked to keep their eye fixated on a stationary point for possibly more than 10 minutes. There have been many attempts to alleviate this problem. The majority of these attempts have focused on the duration of the test. Tests with fewer points and more approximations have been developed. Of course, these tests sacrifice accuracy for a reduction in total test time.

Moving Fixation

Another method introduced to reduce the fatiguing nature of computerized perimetry is a moving fixation point. A moving fixation point means that the eye would also be able to move which would significantly reduce fatigue.

In U.S. Pat. No. 5,035,500 to Rorabaugh et al. (1991), a mechanism is described which allows movement of a fixation point in a visual field test. Although this mechanism may be useful in reducing test fatigue, it suffers from a number of other problems. First of all, the hardware described in this patent is highly specialized. It therefore follows that this equipment will be expensive and not portable.

Secondly, the perimeter described in this patent uses blind spot monitoring as its method of fixation control. Blind spot monitoring involves placing a target stimulus in a patient's blind spot periodically. If the patient sees the target in the blind spot, it is assumed that the patient has lost fixation. If the patient does not see the target in the blind spot, it is assumed that fixation has been maintained.

There are two problems with blind spot monitoring. The first problem is encountered with blind spot monitoring in general. If a patient has a large visual field defect near or surrounding the blind spot it is difficult to locate the blind spot. It is also not necessarily valid to assume that a blind spot target not seen means that fixation was maintained. The blind spot target may have fallen in the visual field defect.

The second problem encountered with blind spot monitoring results from its use with a moving fixation point. Since the blind spot is located approximately 15 degrees from a patient's central vision, it must be possible to place a blind spot target about 15 degrees from the fixation point, no matter where it is on the screen. This means that it is not possible to use a moving fixation point and blind spot monitoring on a smaller screen.

A third problem with the mechanism described in U.S. Pat. No. 5,035,500 to Rorabaugh et al. (1991) is the way in which targets are placed in relation to the fixation point. In fact, they are not actually placed. Instead, a number of targets at fixed locations from the fixation point are moved as a group with the fixation point. When a target is illuminated its actual location in the visual field of the eye is calculated. As a result, this method does not produce a uniform field of targets in the visual field of the eye. In order to obtain a uniform mapping, the target values would have to be interpolated.

Another implementation of a moving fixation point, described in U.S. Pat. No. 4,995,717 to Damato (1991), addresses some of the problems of the mechanism outlined in U.S. Pat. No. 5,035,500 to Rorabaugh et al. (1991). In this implementation, a personal computer is used as the visual field perimeter. Using such a general piece of hardware significantly reduces the cost, improves portability, and addresses the first problem of the previous mechanism.

In addition, the implementation described in U.S. Pat. No. 4,995,717 to Damato (1991) uses a different form of fixation control. As the fixation point moves, the patent is required to keep the fixation point surrounded by a cursor. The cursor is, of course, larger than the fixation point and is controlled by moving the mouse of the personal computer. It is assumed that fixation is maintained while the cursor is surrounding the fixation point. It is assumed that fixation is lost when the cursor is no longer surrounding the fixation point. This method of fixation control avoids the problems of the previous mechanism that were introduced by blind spot monitoring.

Although this implementation has advantages over the previous mechanism, it also has problems. First of all, as with the previous mechanism, targets are placed at fixed locations with respect to the fixation point. The targets are then moved as a group with the fixation point. Again, this procedure results in a nonuniform mapping of the visual field.

Secondly, this method of fixation control requires that the mouse be moved continuously with the fixation point. Such movement of the mouse may be difficult for disabled or elderly people, and those that are not familiar with computers. In this implementation, the patient responds to light stimulus by clicking a mouse button. As a result, test performance may also be affected by the patient's ability to coordinate two manual activities involving the mouse.

Laptop Computers

The use of a personal computer as a visual field perimeter can significantly reduce the cost and increase the use of this important diagnostic tool. In the form of a laptop, visual field perimeters can easily move from physician's offices and hospitals to schools, nursing homes, or even third world countries. Wu et al. (1991) described the use of a laptop computer for glaucoma screening. Quigley et al. (1993) detailed the usefulness of such a system in field tests in East Africa.

Although the perimeters described by Wu et al. (1991) and Quigley et al. (1993) were helpful in screening people for glaucoma, they were less sophisticated and useful than the tests used by most computerized perimeters.

A number of factors have prevented visual field tests of the type used by most computerized perimeters from being adapted to laptop computers. Foremost among these factors is the small screen size. Although the screen size of laptop computers has increased over the years it is likely that the screen size will always be limited by the overall size of the machine itself.

Another factor limiting the use of laptops as perimeters has been the quality of the resolution of the screens. Until recently, screens of the quality capable of animation were not readily available.

The present invention is provided to solve these and other problems.

SUMMARY OF THE INVENTION

The present invention is generally a system for measuring the color visual fields of a patient's eyes. The system includes a viewing area for the patient to direct one of their eyes toward. The viewing area also has a viewing area perimeter, and the viewing area is divided into four substantially equal quadrants.

The system further includes a fixation structure, which is located generally at a central portion of the viewing area. Generally, the purpose of the fixation structure is to hold the attention of the patient.

There are also a plurality of predetermined and substantially linear paths included in the system. The paths extend in directions radially outward from the fixation structure toward the viewing area perimeter. The plurality of predetermined paths are spaced apart by substantially equal angles of separation. Also, each quadrant of the viewing area includes at least two predetermined paths therein.

The system further includes a stimuli target that is configured to continuously and automatically move along the predetermined paths. The stimuli target moves in a direction beginning at a beginning point on the viewing area and continues toward an ending point for each path. The stimuli target completes movement on a first path before beginning movement on a second path.

Additionally, the system includes a patient interface portion for recording the locations within the viewing area where the patient detects a perceived change in color of the stimuli target as it moves along the predetermined paths. The patient indicates the perceived change in color through the patient interface portion which indicates the completion of movement for the stimuli target on an individual path.

In another embodiment of the present invention, the fixation structure may include a central focal target and an orbiting focal symbol to hold the attention of the patient. The system may also include a stimuli target movement portion that allows the patient to move the stimuli target across the viewing area in substantially straight lines and in directions beginning at a beginning point on the viewing area and continuing toward an ending point.

In yet another embodiment of the present invention, the system may include an adjustable headrest assembly that contains both an upper and a lower section. The upper section contains a central aperture and two nose recesses located on either side of the central aperture. The lower section contains two substantially rounded chin recesses which are substantially aligned with the nose recesses. The upper and lower sections are adjustably connected to one another to secure the distance between the nose recesses and the chin recesses.

The system may also include a color change portion for changing the color of the stimuli target in a predetermined order after completion of movement along the individual paths. The color change portion can be automated, and it may alternatively allow the patient to change the color of the stimuli target.

Additionally, the system may include a display portion to convert the color field points into a plot of the resulting color visual field. Also, the stimuli target may be configured to decrease in size as it moves along the individual paths toward the fixation structure. This will give the patient the perception that the stimuli target is the same distance from the eye at all times. However, this is only an option for the present invention, and would not even need to be considered for any future concave computer screen. Therefore, the size of the target can be changed to reflect the changing distance from the target.

Other features and advantages of the invention will be apparent from the following specification taken in conjunction with the following drawings.

DETAILED DESCRIPTION OF THE PREFERRED EMBODIMENT

Figure 1:
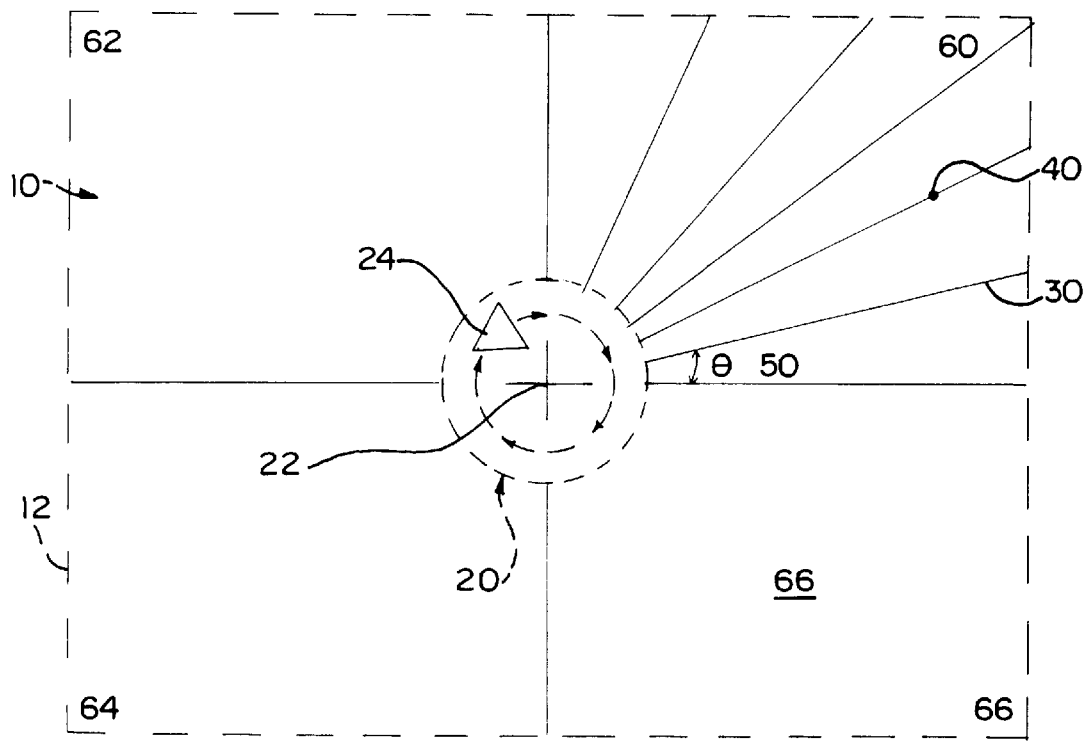
FIG. 1 is one embodiment of the viewing area of a system for measuring color visual fields.

While this invention is susceptible of embodiments in many different forms, there is shown in the drawings and will herein be described in detail a few preferred embodiments of the invention with the understanding that the present disclosure is to be considered as an exemplification of the principles of the invention and is not intended to limit the broad aspect of the invention to the embodiments illustrated.

Figure 16:
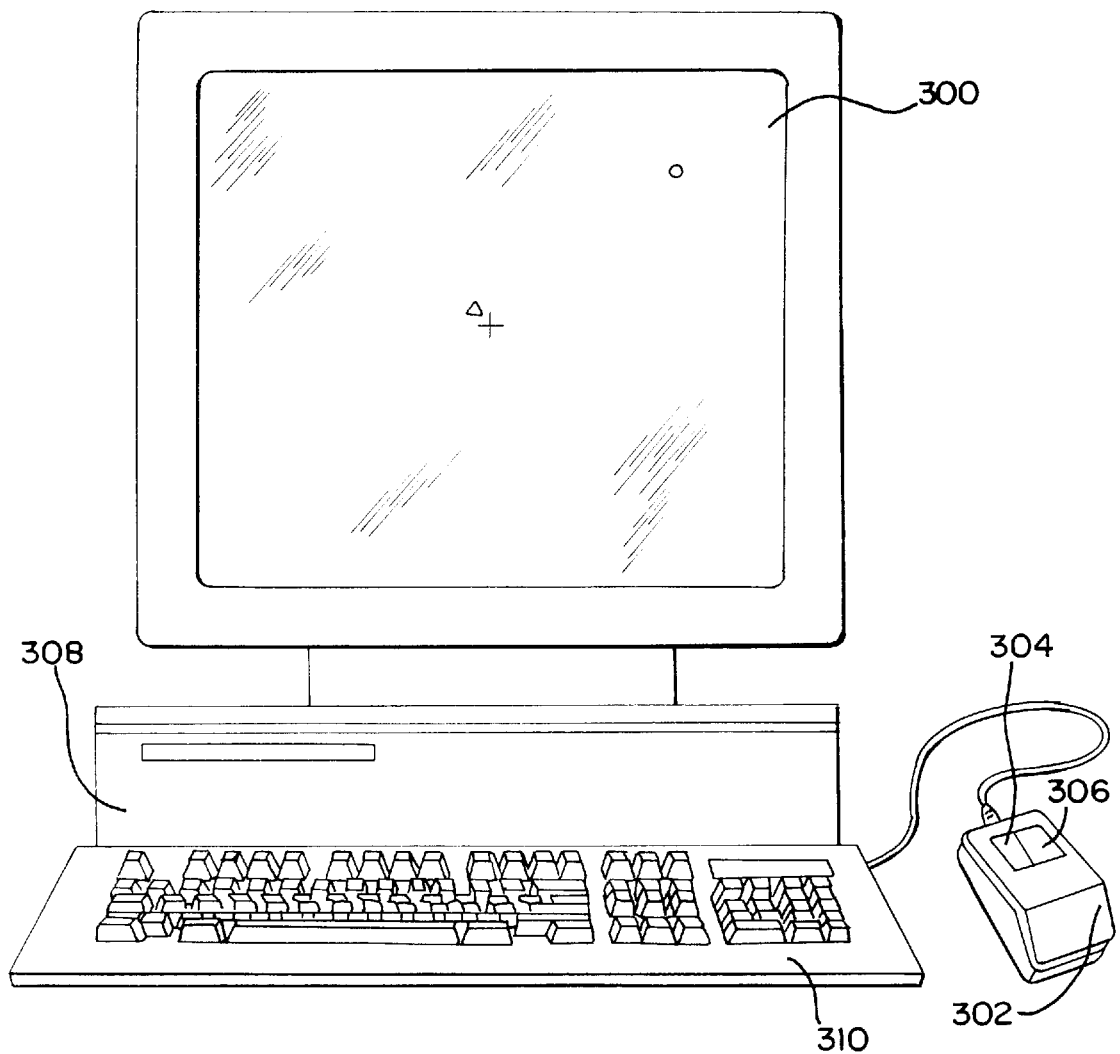
FIG. 16 shows a desktop computer, a display unit, and a mouse.

One embodiment of the system for measuring color visual fields includes a software program that is to be run on either a desktop computer 308 as seen in FIG. 16 or a laptop computer. The software program can be written in a variety of languages to accomplish the same result. A few examples of languages that can be used are: C, C+, C++, and Visual Basic. The peripheral components that are intended to be used in conjunction with the computer 308 are a mouse 302, a keyboard 310, and a monitor 300. The front side of the monitor 300 that faces the user is referred to as the screen or the viewing area 10.

FIG. 1 shows the viewing area 10 of a system for measuring the color visual fields of a patient's eye. A screen of a computer monitor 300 is generally the preferred form of the viewing area 10. The viewing area 10 has a viewing area perimeter 12, which is the perimeter or edges of the screen. It is the viewing area 10 which the patient directs one of their eyes toward. The viewing area 10 is divided into four equal quadrants 60, 62, 64, and 66. These quadrants are for explanation purposes only, and do not actually appear on the viewing area 10.

The fixation structure 20 is located generally at a central portion of the viewing area 10. This central portion is typically the center of the computer screen. The purpose of the fixation structure 20 is to provide an object for the patient to look at or focus on. If the patient looks at the moving stimuli target 40 instead of the fixation structure 20 while taking the test, the results will be invalid. Therefore, continuous fixation on the fixation structure 20 is necessary.

There are limitless types of objects or symbols that can be used as a fixation structure. Simple fixation structures may be comprised of a cross-hair, a small circle, or any other small symbol. The appearance of the fixation structure 20 may change while the patient is taking the test to help prevent symptoms of eye fatigue and ensure the appropriate fixation. Examples of the changes in appearance are changes in the color, size or shape of the object.

One embodiment of the fixation structure 20 would comprise both an orbiting focal symbol 24 and a central focal target 22. The central focal target 22 is positioned at the center of the viewing area 10 and may be in the shape of a cross-hair as shown in FIG. 1, or some other shape. The orbiting focal symbol 24 may be in the shape of a triangle as shown in FIG. 1, or some other shape, and will closely orbit around the central focal target 22. Again, both the central focal target 22 and the orbiting focal symbol 24 may change in appearance to help maintain the attention of the patient. These changes in appearance may include changes in size, shape, and color, such as using a cartoon character for children patients. Further, the central focal target 22 can be larger of smaller than orbiting focal symbol 24, depending on the patient's needs, such as the location of a patient's blind spot. Additionally, the direction of rotation of the orbiting focal symbol 24 may reverse and orbit in the opposite direction. All of these changes to the components of the fixation structure 20 are designed to reduce the symptoms of fatigue and ensure proper fixation of the patient's eye.

The stimuli target 40 is an important component in the system for measuring the color visual fields of a patient's eyes. The software program can be designed in a variety of ways to provide movement of the stimuli target 40 across the viewing area 10. One design is to fully automate the movement of the stimuli target 40 along a plurality of predetermined substantially linear paths 30. These paths 30 extend in directions radially outward from the fixation structure 20 toward the viewing area perimeter 12. The predetermined paths 30 are spaced apart by substantially equal angles 50 of separation. Each quadrant of the viewing area 10 should include at least two predetermined paths 30 therein. This means that there should be at least eight predetermined paths 30 in the system. While results could be obtained using fewer paths 30, the resulting mappings of the color fields would be vague and unhelpful to a doctor interpreting the results. It is likewise true that the more predetermined paths 30 that are used, the more detailed and informative the resulting plots of the color fields will be. For example, if the predetermined paths 30 are spaced apart by fifteen degree increments, then there will be a total of twenty four individual paths 30 in the viewing area 10. However, the attention span of the patent becomes a factor in the number of paths being used.

The software program may provide movement of the stimuli target 40 along the predetermined paths 30. The stimuli target 40 is configured to automatically move in a slow and continuous fashion along the predetermined paths 30. The stimuli target 40 moves in a direction beginning at a beginning point on the viewing area 10 and continuing toward an ending point for each path. The preferred direction of movement is from a beginning point at the viewing area perimeter 12 and continuing along a path 30 toward the fixation structure 20 or the ending point. Movement of the stimuli target 40 in a direction toward the fixation structure 20 is the preferred direction, however, movement in the opposite direction may also be permitted.

Movement of the stimuli target 40 on the first path is to be completed before the stimuli target 40 begins movement on a second path, and likewise for all subsequent paths. Completion of movement of the stimuli target 40 results when the patient perceives a change in color of the stimuli target 40 or in the alternative, when the stimuli target 40 reaches the fixation structure 20 without the patient having detected any change in color.

A patient interface portion is also provided to record the locations within the viewing area 10 where the patient detects a perceived change in color of the stimuli target 40 as it moves along the predetermined paths 30. These locations are referred to as color field points and are saved in the computer 308 for future uses, such as graphing and plotting, or comparing different tests of the same patient or other patients to one another. The patient interface portion also provides a way for the patient to indicate the perceived change in color which indicates the completion of movement for the stimuli target 40 on an individual path 30. Once movement of the stimuli target 40 is completed on a path, the stimuli target will automatically jump to another path and begin movement on that path.

The system can also include a color change portion for changing the color of the stimuli target 40. The color change portion can be automated through the software to automatically change the color of the stimuli target 40 in a predetermined order after completion of movement along individual paths. While a variety of different color fields can be taken, the most important color fields to map are red, green, blue, and white. The color change portion can take one color field at a time by keeping the stimuli target 40 the same color and completing movements along all of the paths in the viewing area 10 before changing the stimuli target to a different color. The color change portion can also be programmed to take multiple color fields simultaneously by changing the color of the stimuli target 40 after completion of movement on each path, by either a predetermined or a random sequence, until complete color fields have been taken for all of the colors.

The color change portion need not be completely automated, for it may provide for allowing the patient to change the color of the stimuli target 40. This is achieved by allowing the patient to press the right mouse button 306 on the mouse 302 and choose the desired color for the stimuli target 40. The ability to change colors, as well as the hues of the colors, of the stimuli target 40 is available at any time, including at the beginning, the middle, and the end of movement along a path 30.

The system also may include a display portion to convert the individual locations where the patient detects perceived changes in color of the stimuli target 40 into a plot of the resulting color visual field. As previously mentioned, the locations where the patient detects perceived changes in color of the stimuli target 40 are referred to as color field points. The software program saves the locations of the color field points by recording their X and Y coordinates on an X-Y coordinate system. Once all of the color field points for a particular color have been recorded, the program is then able to plot all of the color field points on the viewing area 10 or a peripheral printer. The program then interpolates the color field points with a line to produce a completed color field mapping. The program is also capable of displaying only the interpolated field (typically a line from point to point), and hiding the color field points. Multiple color field mappings are also capable of being displayed simultaneously.

Complex visual effects may be achieved by altering the size of the stimuli target 40 as it moves across the viewing area 10. By decreasing its size as it moves along the individual paths 30 toward the fixation structure 20, it will appear to patient as if it is the same distance form the eye at all times, based on the viewing area being a substantially flat surface. If the stimuli target 40 is in the shape of a small circle, then the program can simply reduce its diameter as it approaches the center of the viewing area 10.

The software program may also provide movement of the stimuli target 40 in a less automated design. In this stimuli target movement portion, the patient is allowed to move the stimuli target 40 across the viewing area 10. Movement of the stimuli target 40 is controlled by moving the mouse 302. The stimuli target 40 should be moved in directions beginning at a beginning point on the viewing area 10 and continuing toward an ending point. Movement is possible in any direction, but the preferred direction should begin at the viewing area perimeter 12 and continue toward the fixation structure 20. For best results, the patient should move the stimuli target 40 at a slow and steady speed and in substantially straight lines.

The patient interface portion for this less automated design provides for recording the locations within the viewing area 10 where the patient detects a perceived change in color of the stimuli target 40 as it moves from a beginning point on the viewing area 10 toward the ending point. As mentioned, this should be in a direction toward the fixation structure 20. The patient interface portion also records the plurality of color field points which represent the locations on the viewing area 10 where the patient indicates the perceived change in color of the stimuli target 40 by pressing the left mouse button 304 on the mouse 302. The display portion for this design also converts the color field points into a plot of the resulting color visual field. All of the options mentioned for the design utilizing the predetermined paths 30 may also be included in this embodiment.

The system can also include an adjustable headrest assembly as shown in FIGS. 2–15. The headrest assembly contains and upper section 100 and a lower section 110. The upper section 100 contains a central aperture 102 for the patient's eye to look through. The upper section 100 also contains two nose recesses 104 which are located on both sides of the central aperture 102. These nose recesses 104 are designed to fit snugly and comfortably over the patient's nose. The lower section 110 contains two substantially rounded chin recesses 114 which are substantially aligned with the nose recesses 104. These chin recesses 114 fit comfortably under the patient's chin to hold the patient's head steady. The upper section 100 and the lower section 110 are adjustably connected to one another to secure the distance between the nose recesses 104 and the chin recess 114.

The upper section 100 and the lower section 110 of the headrest assembly are adjusted with respect to one another to closely fit over the patient's nose and under the patient's chin to substantially prevent the patient's head from moving and to hold the patient's eye in alignment with the central aperture 102 and the fixation structure 20. The headrest assembly should be adjustably positioned at a distance from the viewing area 10 while maintaining horizontal and vertical alignment of the central aperture 102 with the fixation structure 20. The minimum and prefered suggested distance for the headrest position from the viewing area is about eight (8) inches with a standard 17 inch (diagonally measured as 15 and ¾ inches) Sony Trinitron Molesan 17SFII screen. However, doubling the eight (8) inch minimun/preferred distance from the screen would require doubling the area of the screen. Proportions of these ratios in between and outside of these two arrangements also apply.

Figure 2:
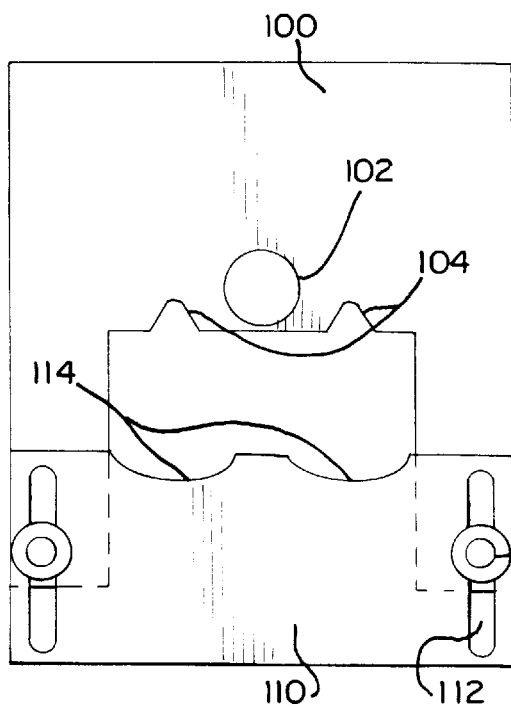
FIG. 2 is a front view of one embodiment of a two piece headrest assembly of the present invention.
Figure 3:
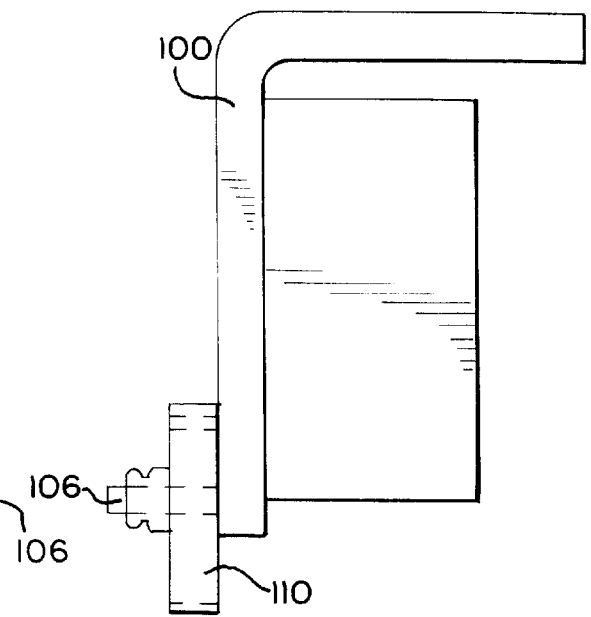
FIG. 3 is a right-side view of the embodiment from FIG. 2 of the present invention.

FIG. 2 shows a front view of a two piece headrest assembly, and FIG. 3 shows a right side view of the same headrest assembly. The upper section 100 and the lower section 110 of this assembly are connected by threaded bracket protrusions 106 which are fixed to the upper section 100 and pass through the bracket slots 112 in the lower section 110. Wingnuts or hexagonal nuts may be used to then secure the two sections together.

Figure 5:
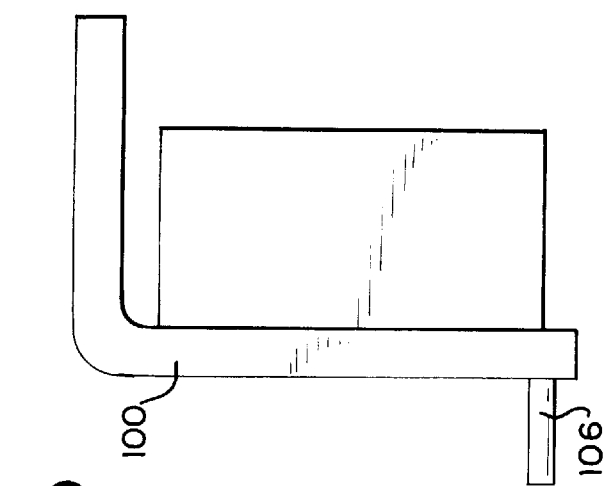
FIG. 5 is a right side view of the top section of the embodiment from FIG. 2 of the present invention.
Figure 7:
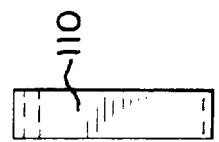
FIG. 7 is a right side view of the bottom section of the embodiment from FIG. 2 of the present invention.
Figure 4:
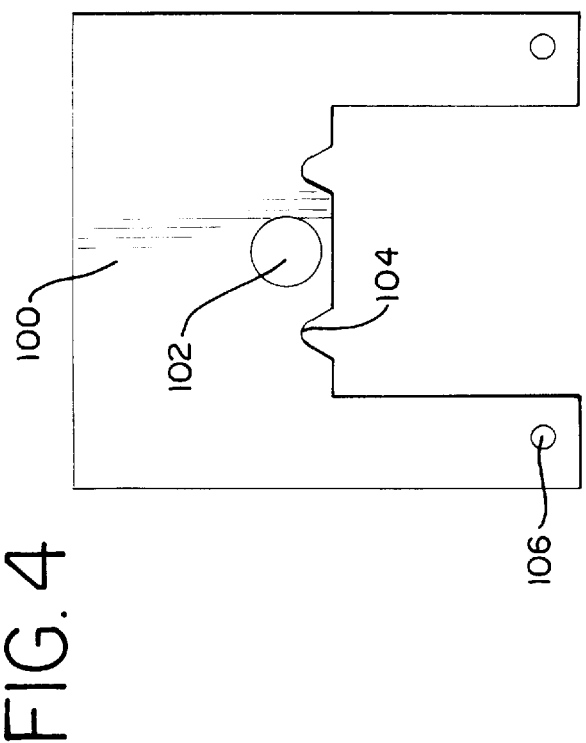
FIG. 4 is a front view of the top section of the embodiment from FIG. 2 of the present invention.
Figure 6:
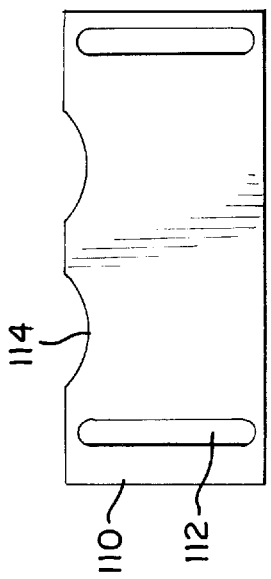
FIG. 6 is a front view of the bottom section of the embodiment from FIG. 2 of the present invention.

FIG. 4 shows a front view of the upper section 100 of an unconnected two piece headrest assembly. FIG. 5 shows a right side view of the same upper section 100. FIG. 6 shows a front view of the lower section 110 of an unconnected two piece headrest assembly. FIG. 7 shows a right side view of the same lower section 110. These figures more clearly depict the protrusions 106 which are fixed to the upper section 100 and the bracket slots 112 in the lower section 110.

Figure 11:
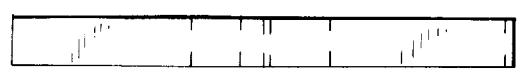
FIG. 11 is a right side view of the top section of the embodiment from FIG. 8 of the present invention.
Figure 13:
FIG. 13 is a right side view of the bottom section of the embodiment from FIG. 8 of the present invention.
Figure 10:
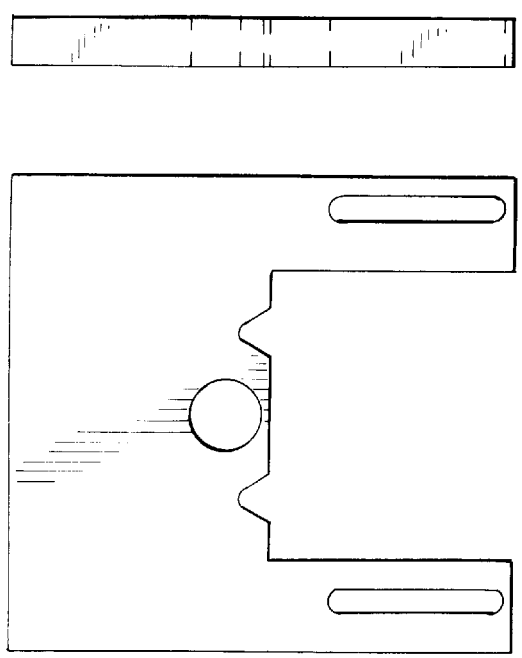
FIG. 10 is a front view of the top section of the embodiment from FIG. 8 of the present invention.
Figure 12:
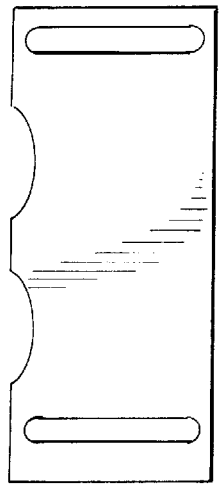
FIG. 12 is a front view of the bottom section of the embodiment from FIG. 8 of the present invention.
Figure 15:
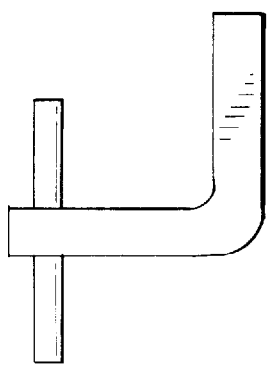
FIG. 15 is a right side view of the distance bracket of the embodiment from FIG. 8 of the present invention.
Figure 9:
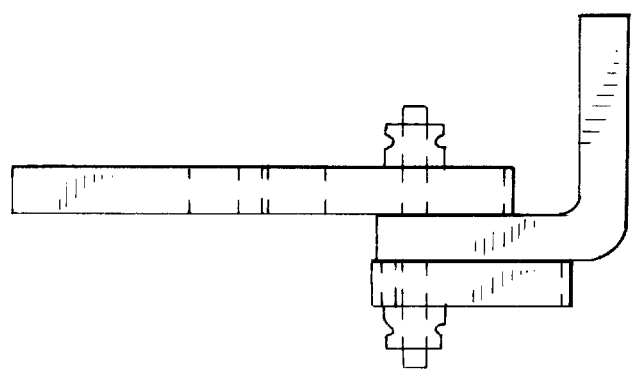
FIG. 9 is a right-side view of the embodiment from FIG. 8 of the present invention.
Figure 14:
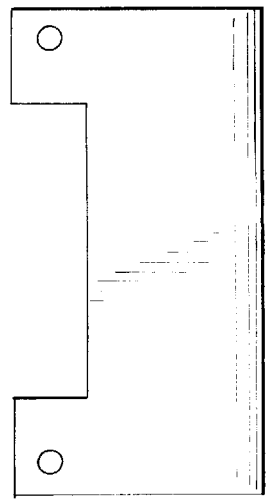
FIG. 14 is a front view of the distance bracket of the embodiment from FIG. 8 of the present invention.
Figure 8:
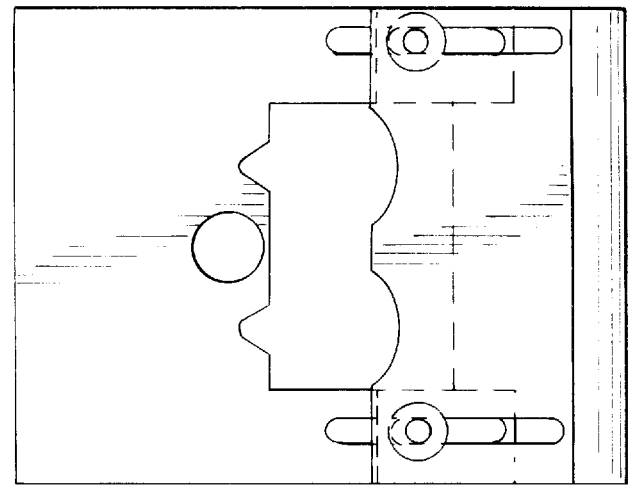
FIG. 8 is a front view of one embodiment of a three piece headrest assembly of the present invention.

FIGS. 8–15 illustrate a three piece headrest assembly, which is a modification of the two piece headrest assembly. The front view of the connected three piece assembly is shown in FIG. 8. FIG. 9. is a right side view of the headrest assembly shown in FIG. 8. FIG. 10 is the front view of the upper section of the three piece assembly and FIG. 11 is a right side view of the same component. FIG. 12 is the front view of the lower section and FIG. 13 is a right side view of the lower section. The lower headrest assemblies, as shown in FIGS. 2, 6, 7, 8, 12, and 13 are all identical for both the two and three piece headrest assembly. FIG. 14 is a front view of the headrest connector, and FIG. 15 is a right side view of the same component. The upper section 100 in the two piece headrest design has threaded bracket protrusions 106 fixed to it, where the upper section in the three piece design does not have these bracket protrusions. Instead, the upper section in FIG. 10 has elongated bracket slots similar to those found in the lower section. It is the headrest connector component in the three piece headrest assembly design that has the threaded bracket protrusions fixed to it. These bracket protrusions are fixed to the connector component and extend horizontally in opposite directions. These bracket protrusions then pass through the bracket slots in both the upper section and lower section and are secured with wingnuts or hexagonal nuts. The headrests mentioned above can be directly connected or mounted to the screen (viewing area) or a stand alone apparatus.

Figure 17:
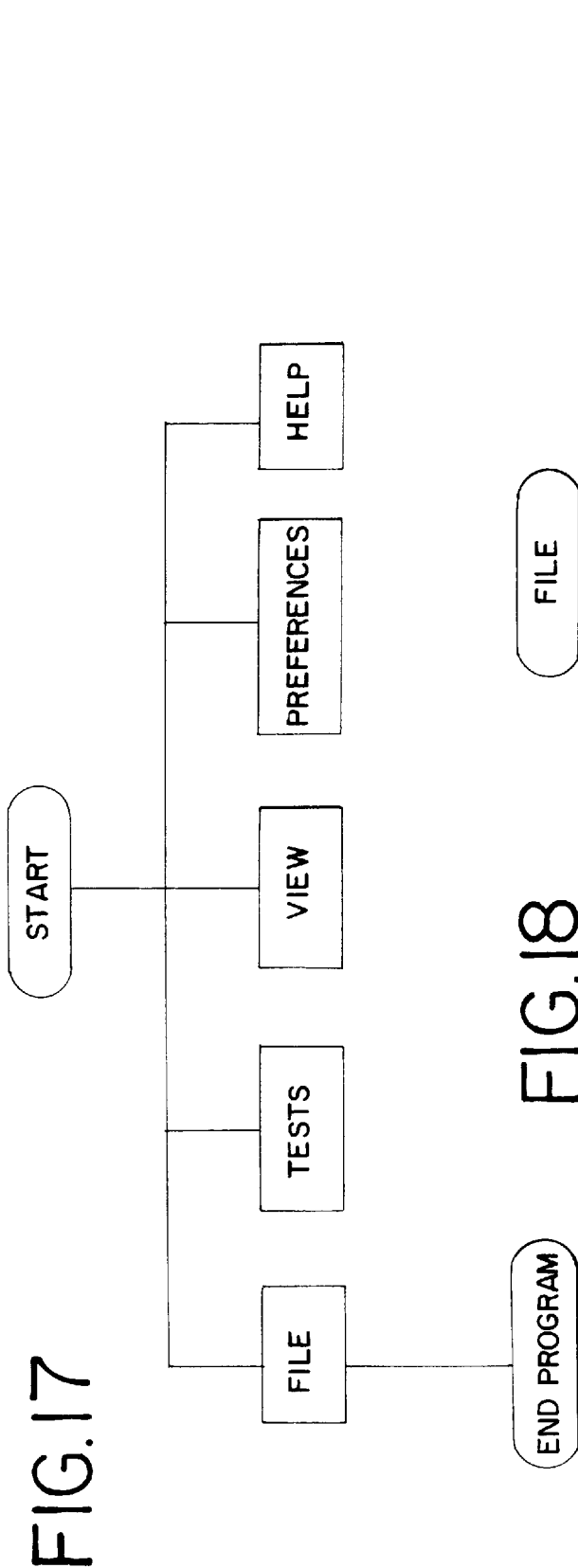
FIG. 17 is a flow chart showing the main options available in the program.

The main options or subroutines available in the preferred software is outlined in FIG. 17. The options as outlined are: File, Tests, View, Preferences, and Help. Each of these options are headings for pull down menus that list additional user options. Other options can also be a part of the present invention, such as a built-in tutorial. The tutorial can include a virtual doctor (computer generated doctor or a digital video reproduction of an actual doctor) appearing on the screen, and the virtual doctor would then direct the patient in taking the test. Thus, the apparatus could be configured so that most or all anticipated questions that a patient might have could be answered through an answer from the virtual doctor.

Figure 18:
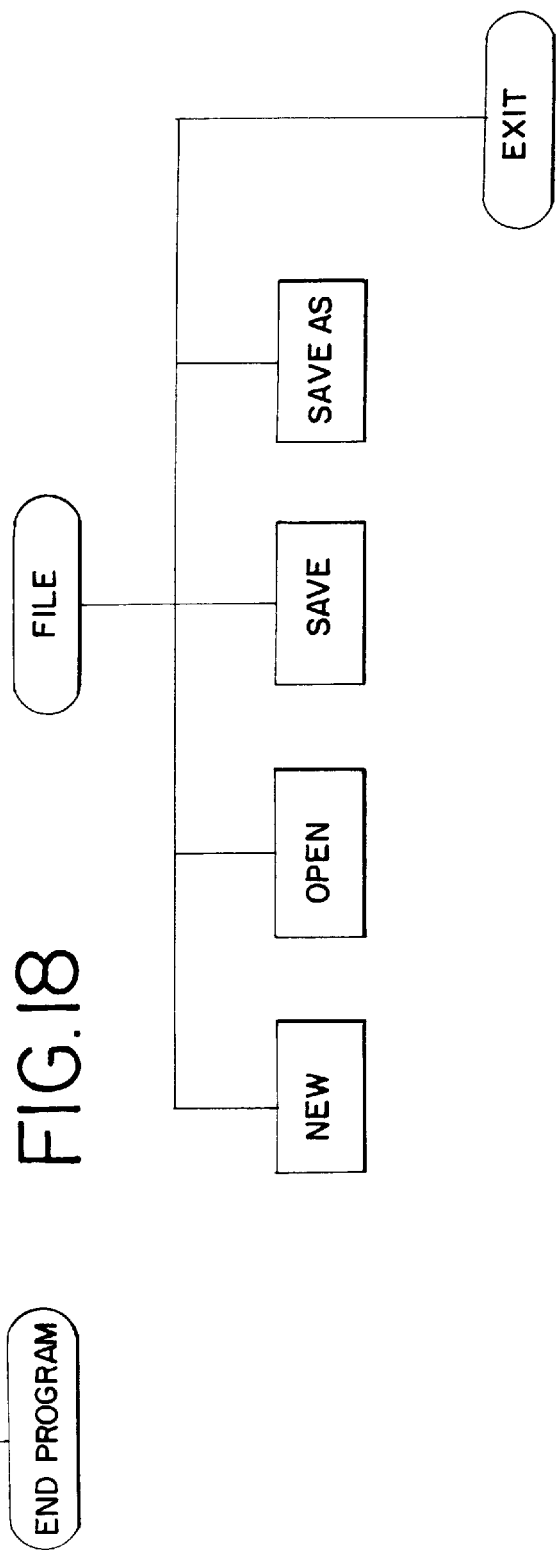
FIG. 18 is a flow chart showing the options available in the "File" subroutine.

FIG. 18 shows the options available under the File heading. These options are: New, which allows a user to create a new patient file; Open, which allows the user to open an existing file; Save, which allows a user to save a file; Save As, which enables a user to save a file under a new name or in a different directory; and Exit, which allows the user to exit from the program.

Figure 19:
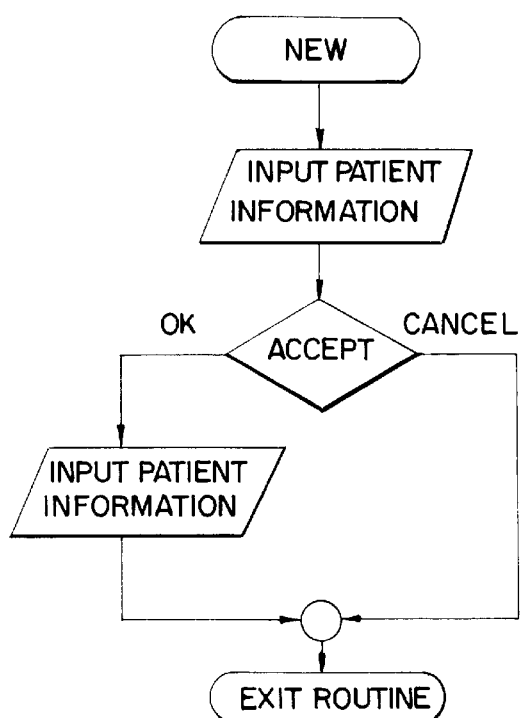
FIG. 19 is a flow chart showing the steps of adding new patient information.

The New command is outlined in FIG. 19 and allows the user to input new patient information and then either accept and input the patient information into a database or cancel and exit the subroutine.

Figure 20:
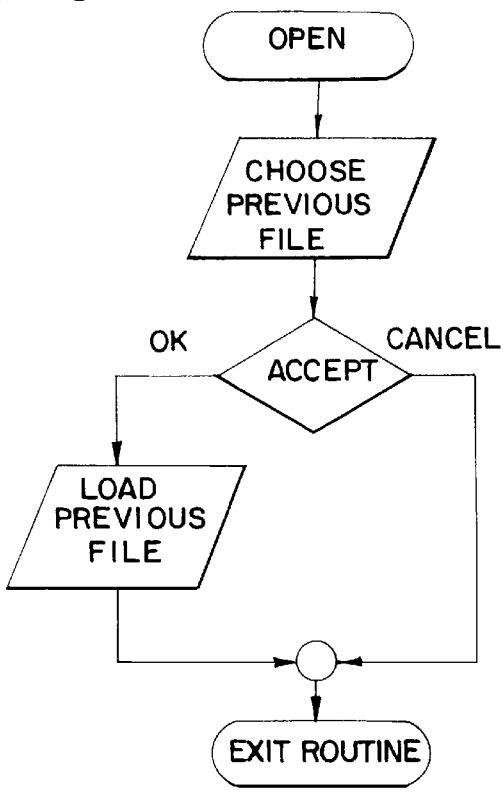
FIG. 20 is a flow chart showing the steps of opening an existing patient's file.

FIG. 20 outlines the Open command. Here, the user is permitted to choose a previous file to open. The user may then accept and load the previous file or cancel and exit the subroutine.

Figure 21:
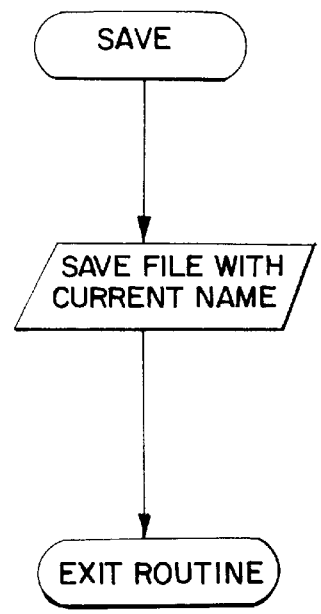
FIG. 21 is a flow chart showing the steps of saving a file.

FIG. 21 is an outline of the Save command which enables the user to save the present file with its current file name and then exit the subroutine.

Figure 22:
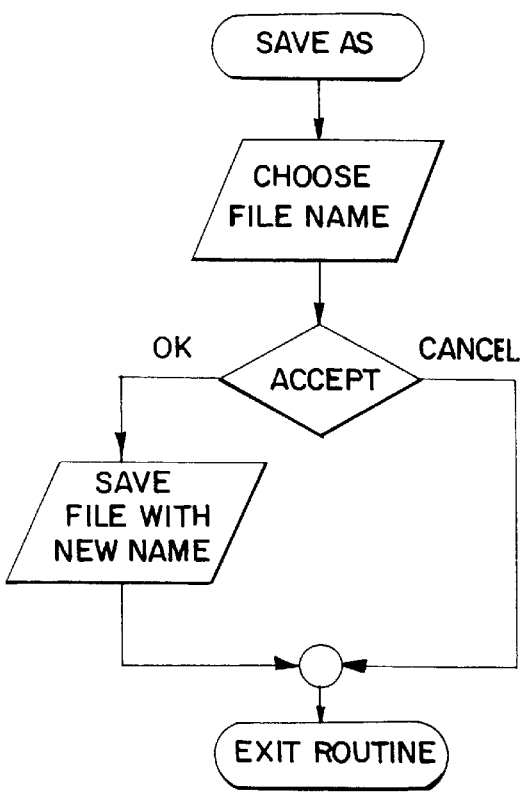
FIG. 22 is a flow chart showing the steps of saving a file with a different name.

The Save As command is outlined in FIG. 22. This subroutine enables the user to choose a file name and directory to save a file with, or the cancel the command and exit the subroutine.

Figure 23:
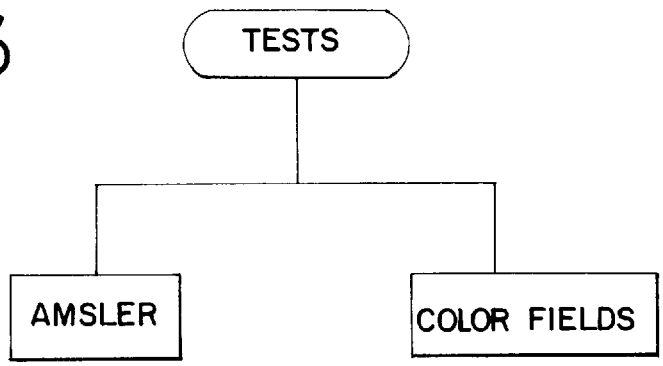
FIG. 23 is a flow chart showing the different tests available to select.

The Test options that are available in the preferred software are outlined in FIG. 23. These options are an Amsler test and a Color Fields test.

Figure 24:
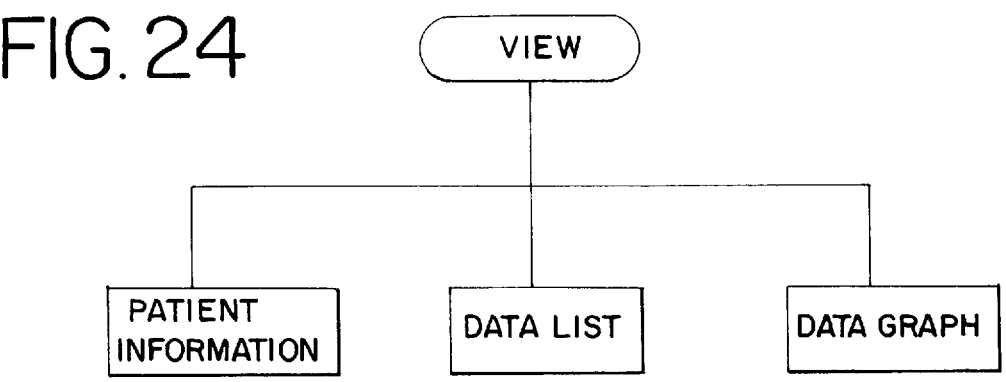
FIG. 24 is a flow chart showing the options that are available to view.

FIG. 24 outlines the options available under the View heading. These options include viewing the Patient Information, viewing a Data List of the patient data, and viewing a Data Graph of the patients color field mappings.

Figure 25:
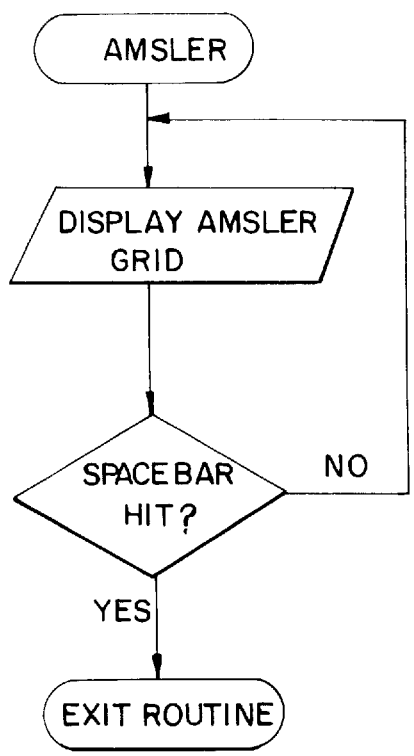
FIG. 25 is a flow chart that explains the display of the Amsler Grid.

An outline of the Amsler test is given in FIG. 25. When the Amsler test is selected, the software displays an Amsler Grid and enables a patient to take an Amsler test. The Amsler grid and test allows for detection of holes in the retina, detection of fluid leakage due to hypertension, as well as detection of the blind spot and other blind spot. When the patient views the grid with one eye, the ability of the patient, while focusing on the center of the grid, to peripherally see all of he lines of the grid will determine the physical structure and health of the patient's eye, as shown by the examples provided above. In particular, the patient seeing wary lines, the non-existence of lines, or hemispheres may indicate the health and/or structure of the eye.

Figure 26:
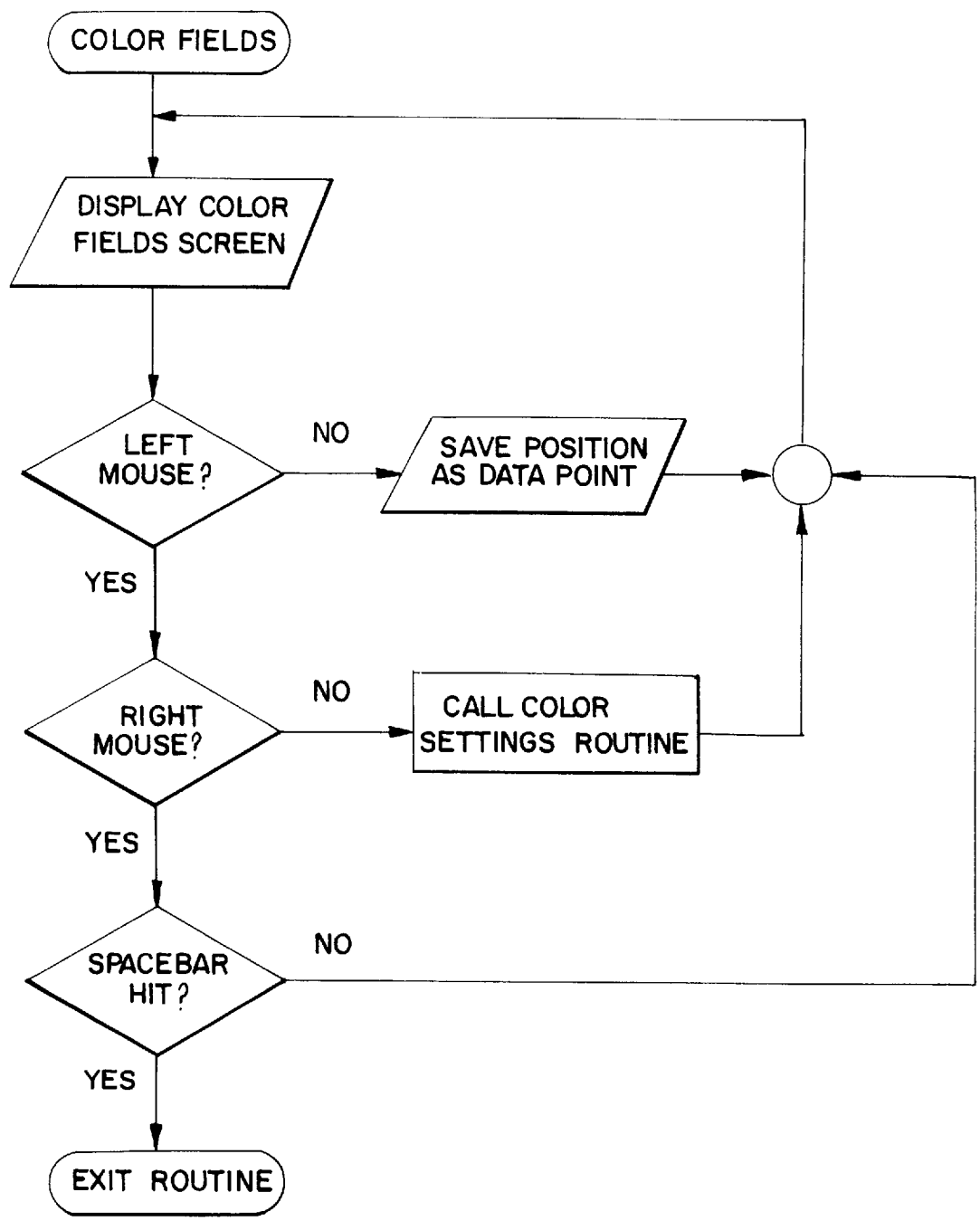
FIG. 26 is a flow chart showing the steps of taking a color fields test.

FIG. 26 is an outline of the subroutine for the Color Fields test. After selecting the Color Fields test, the Color Fields Screen is displayed and the test may begin. The preferred software program will monitor inputs received from the mouse 302. If the left mouse button 304 is pressed, then a color field point is created and the data is recorded by the program. If the right mouse button 306 is pressed, then the Color Settings subroutine is brought up and activated. The program will also monitor the keyboard 310 so that when the spacebar is pressed the subroutine is ended and the program takes the user back to the starting menu outlined in FIG. 17.

As a side issue, once the Amsler test is run, the patient and/or doctor may have an idea of where the blind spot or other inability to peripherally see, may exist. The patient, operator, or doctor can then switch over to the Color Fields test and manually use the target to vertically and horizontally move through these blind spots. During these movements, the boundaries of these blind spot areas can be recorded by pressing the right mouse button to create points at the boudaries (point at which the patient detects the existence or disappearance of the target). Thus, a plurality of blind spot boundary points are created and can be plotted to display the blind spot area, including the actual blind spots and any other areas where the patient is unable to peripherally see. The display can be plotted with the color fields of the Color Fields test.

Figure 27:
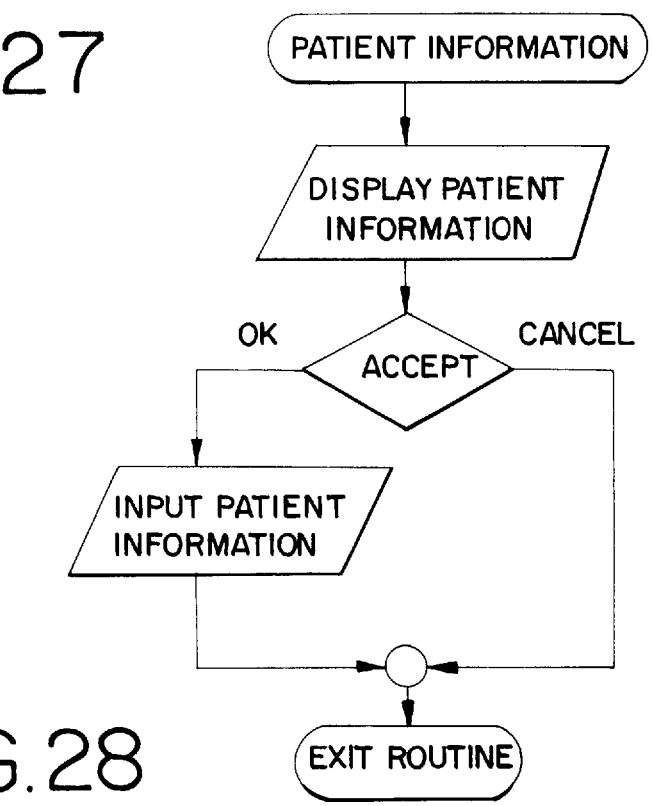
FIG. 27 is a flow chart showing the options available in entering patient information.

The Patient Information subroutine is outlined in FIG. 27. This routine allows the user to display the Patient Information screen. This enables a user to view and modify an existing patient's information, or to input information on a new patient. The information can then be saved or the user may cancel the routine and return to the starting menu.

Figure 28:
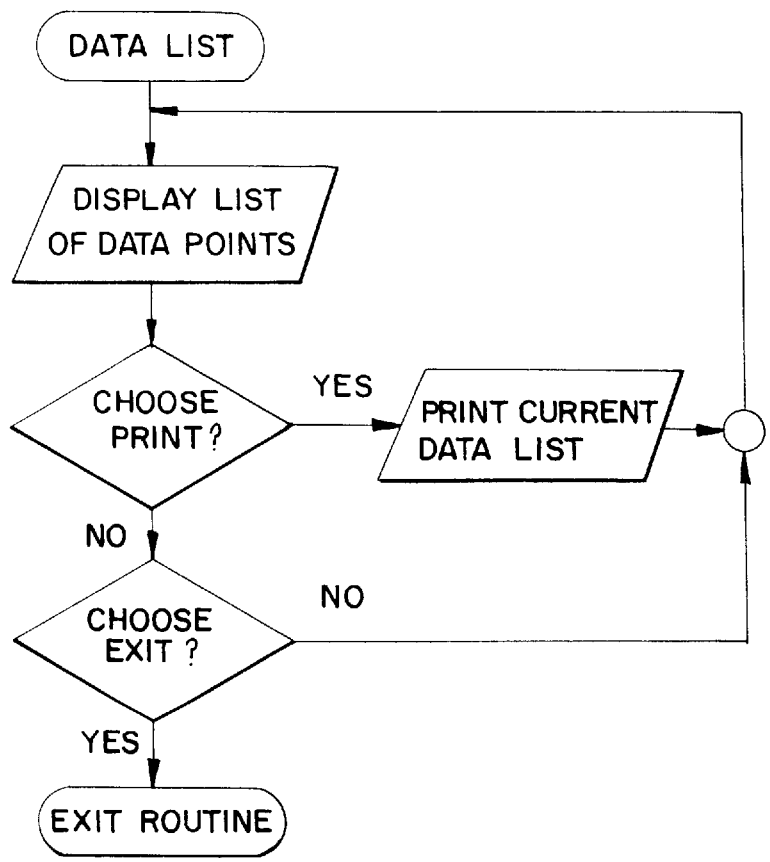
FIG. 28 is a flow chart showing the options available in displaying a list of data points.

A program outline of the Data List subroutine of the preferred software is shown in FIG. 28. This routine enables a user to display a list of all of the X and Y coordinates of the color field points taken in a color field test. This list may include data for each color field that was mapped. The user is also given an option to print the current data list or to exit the subroutine.

Figure 29:
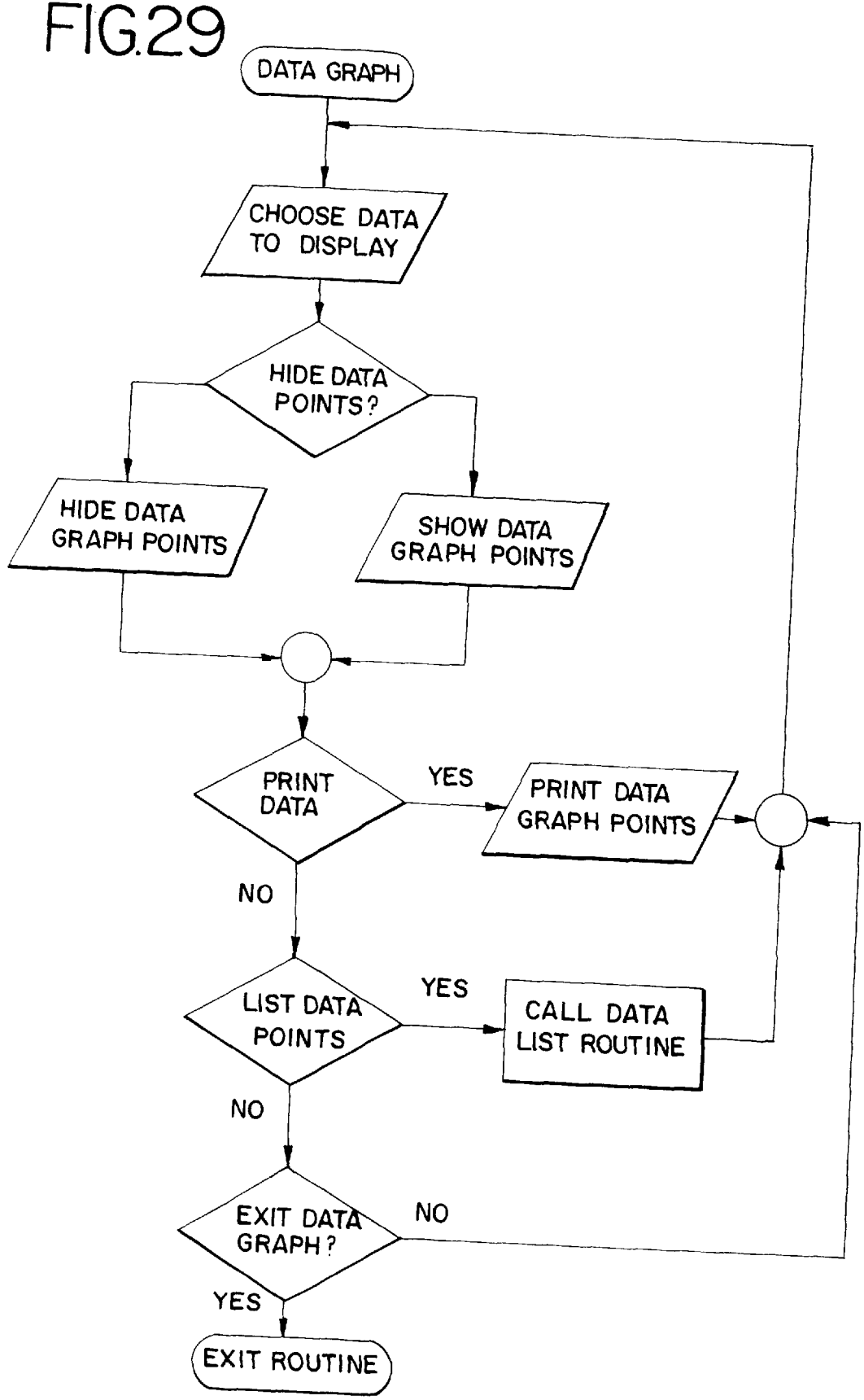
FIG. 29 is a flow chart showing the options available in displaying a graph of the color field points.

FIG. 29 is an outline of the Data Graph subroutine.

The user is permitted to choose which of the color field mappings they would like to display. More than one mapping can be displayed simultaneously on the viewing area 10. The user is also given the option to either hide or display the color field points. Additionally, the user is given the option to print the Data Graph points, which are the same as the color field points. The user may also call the Data List routine to view a list of the data points, or they may choose to exit the Data Graph subroutine.

Figure 30:
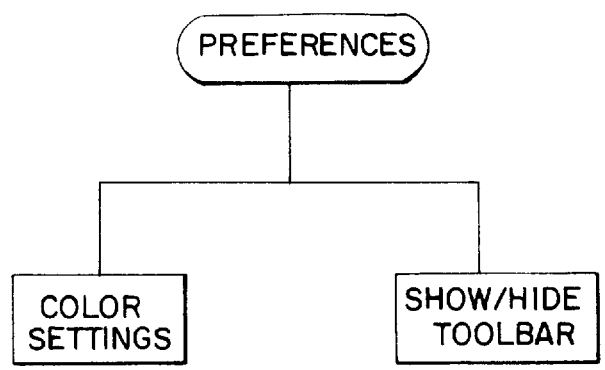
FIG. 30 is a flow chart showing the "Preferences Options" that are available.

The outline for the Preferences options is given in FIG. 30. Here, the user is given the option to select the Color Settings routine or the Toolbar routine.

Figure 31:
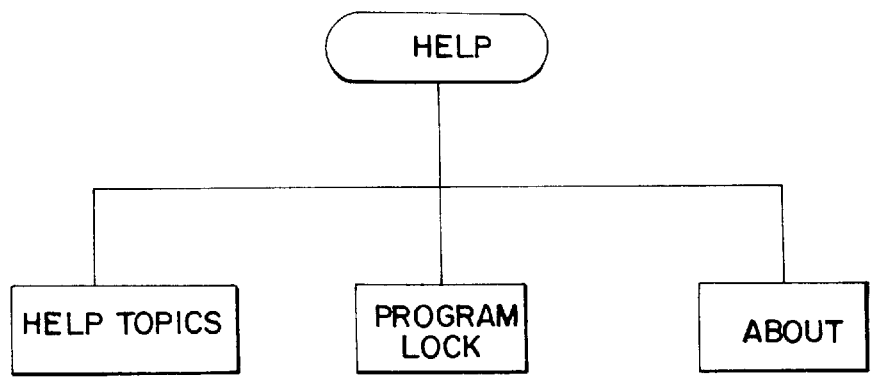
FIG. 31 is a flow chart showing the help options that are available.

The Help options that the preferred software has made available to a user is shown in FIG. 31. The user may select from a Help Topics routine, a Program Lock routine, or an About routine.

Figure 32:
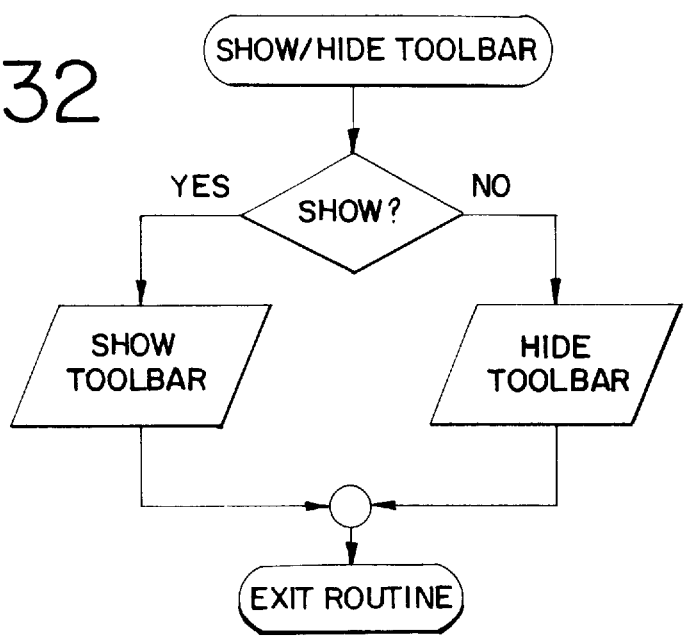
FIG. 32 is a flow chart showing the toolbar options.

FIG. 32 shows the outline for the Toolbar subroutine. This routine gives a user the option to either show or hide the toolbar.

Figure 33:
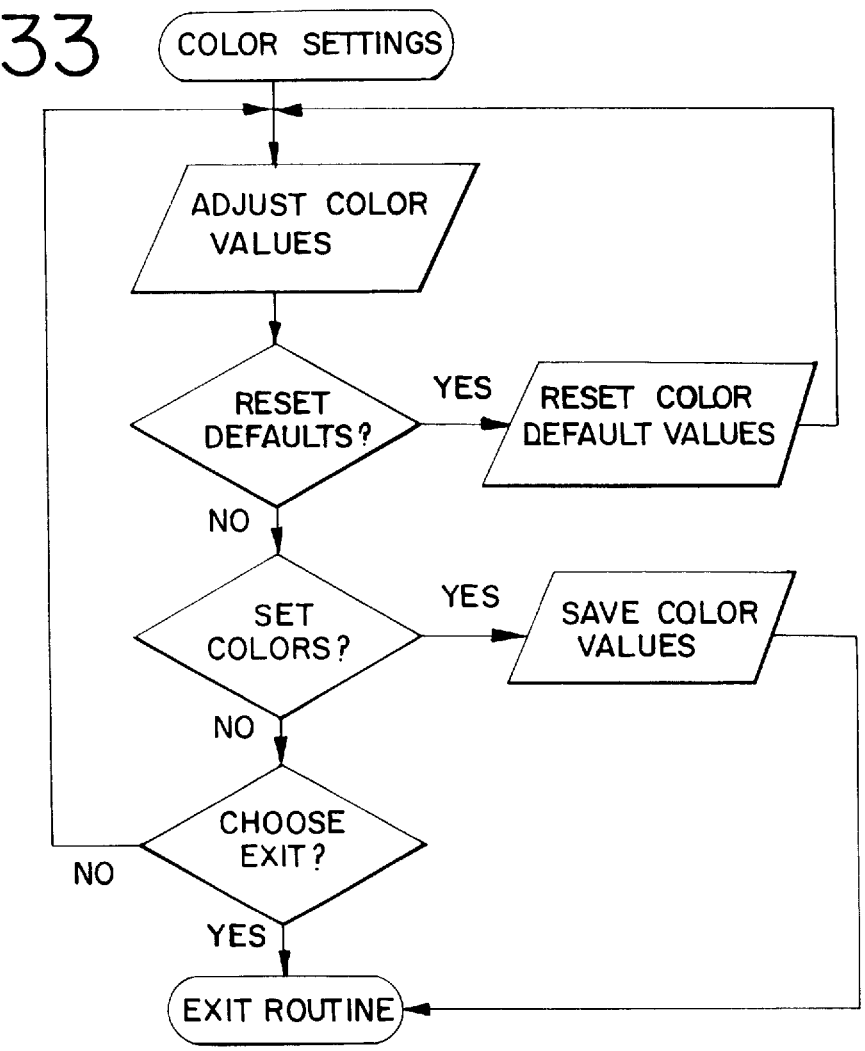
FIG. 33 is a flow chart showing the color settings options.

FIG. 33 is the outline of the Color Settings subroutine. This routine enables the user to adjust the color values to be used on the stimuli target 40 or to reset the color values to their default settings.

Figure 34:
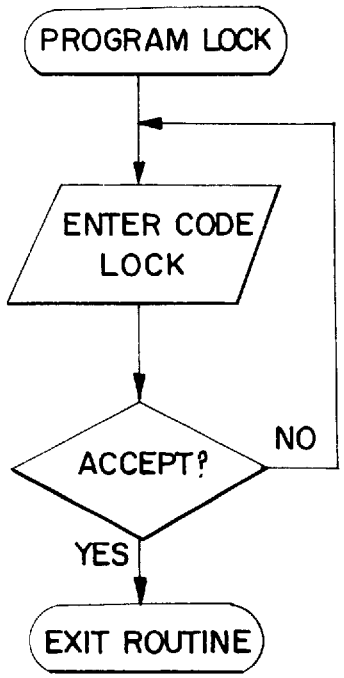
FIG. 34 is a flow chart explaining the "Program Lock" command.

The subroutine for the Program Lock command is shown in FIG. 34. This routine enables the user to lock or unlock the program. When unlocking the program, the routine prompts the user to enter a code, and then accepts or rejects the code based on its accuracy.

Figure 35:
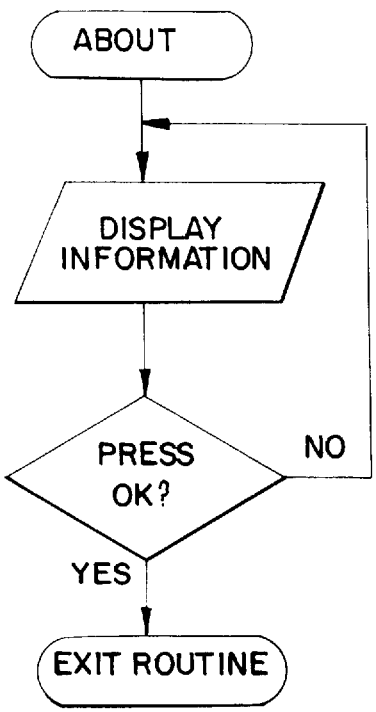
FIG. 35 is a flow chart explaining the "About" command.

The About command is outlined in FIG. 35 and enables the user to display information about the inventors and developers of the system.

While the specific embodiments have been illustrated and described, numerous modifications come to mind without significantly departing from the spirit of the invention, and the scope of protection is only limited by the scope of the accompanying Claims.

What we claim is:

1. A system for measuring color visual fields of a patient's eyes, comprising:
    a viewing area for the patient to direct one of their eyes toward, wherein the viewing area has a viewing area perimeter and is divided into four substantially equal quadrants;
    a fixation structure located generally at a central portion of the viewing area to hold the attention of the patient;
    a plurality of predetermined substantially linear paths, extending in directions radially outward from the fixation structure toward the viewing area perimeter, wherein the plurality of predetermined paths are spaced apart by substantially equal angles of separation, and wherein each quadrant of the viewing area includes at least two predetermined paths therein;
    a stimuli target configured to continuously and automatically move along the predetermined paths in a direction beginning at a beginning point on the viewing area and continuing toward an ending point for each path, wherein the stimuli target completes movement on a first path before beginning movement on a second path; and,
    a patient interface portion for recording the locations within the viewing area where the patient detects a perceived change in color of the stimuli target as it moves along the predetermined paths, and wherein the patient indicates the perceived change in color through the patient interface portion which indicates that completion of movement for the stimuli target on an individual path.

2. The system of claim 1 including a color change portion for changing the color of the stimuli target in a predetermined order after completion of movement along individual paths.

3. The system of claim 1, wherein the plurality of predetermined paths are spaced apart by 15 degree increments, having a total of twenty four individual paths in the viewing area.

4. The system of claim 1, including a display portion to convert the individual locations where the patient detects perceived changes in color into a plot of the resulting color visual field.

5. The system of claim 1, wherein the stimuli target decreases in size as it moves along the individual paths toward the fixation structure to give the patient the perception that the stimuli target is the same distance from the eye at all times.

6. A system for measuring color visual fields of a patient's eyes, comprising:
    a viewing area for the patient to direct one of their eyes toward, wherein the viewing area has a viewing area perimeter and is divided into four substantially equal quadrants;

a fixation structure located generally at a central portion of the viewing area, wherein the structure has a central focal target and an orbiting focal symbol to hold the attention of the patient;

a stimuli target movement portion that allows the patient to move a stimuli target across the viewing area in substantially straight lines and in directions beginning at a beginning point on the viewing area and continuing toward an ending point; and, a patient interface portion for recording the locations within the viewing area where the patient detects a perceived change in color of the stimuli target as it moves from the beginning point on the viewing area toward the ending point, and wherein the patient indicates the perceived change in color through the patient interface portion, thereby creating a plurality of color field points representing the locations within the viewing area.

7. The system of claim 6 including a color change portion for allowing the patient to change the color of the stimuli target.

8. The system of claim 6, wherein the appearance of the orbiting focal symbol changes.

9. The system of claim 6, wherein the appearance of the central focal target changes.

10. The system of claim 6, wherein the orbiting focal symbol changes direction of rotation around the central focal target.

11. The system of claim 6, including a display portion to convert the color field points into a plot of the resulting color visual field.

12. The system of claim 6, wherein the stimuli target decreases in size as it moves along the individual paths toward the fixation structure to give the patient the perception that the stimuli target is the same distance from the eye at all times.

13. A system for measuring color visual fields of a patient's eyes, comprising:

an adjustable headrest assembly containing an upper section and a lower section, wherein the upper section contains a central aperture and two nose recesses located on either side of the central aperture, wherein the lower section contains two substantially rounded chin recesses substantially aligned with the nose recesses, wherein the upper and lower sections being adjustably connected to one another to secure the distance between the nose recesses and the chin recesses;

a viewing area for the patient to direct one of their eyes toward, wherein the viewing area has a viewing area perimeter and is divided into four substantially equal quadrants;

a fixation structure located generally at a central portion of the viewing area to hold the attention of the patient, wherein the central aperture of the headrest assembly is substantially aligned with the fixation structure and is adjustably positioned at a distance from the viewing area;

a stimuli target movement portion that allows the patient to move the stimuli target across the viewing area in directions beginning at a beginning point on the viewing area and continuing toward the fixation structure; and, a patient interface portion for recording the locations within the viewing area where the patient detects a perceived change in color of the stimuli target as it moves from the beginning point on the viewing area toward the ending point, and wherein the patient indicates the perceived change in color through the patient interface portion.

14. The system of claim 13, wherein the upper and lower sections of the headrest assembly are adjusted with respect to one another to closely fit over the patient's nose and chin to substantially prevent the patient's head from moving and to hold the patient's eye in alignment with the central aperture and the fixation structure.

15. The system of claim 13, wherein the upper and lower sections are connected by threaded bracket protrusions fixed to the upper section and bracket slots in the lower section.

16. The system of claim 13 including a color change portion for allowing the patient to change the color of the stimuli target.

17. The system of claim 13, including a display portion to convert the color field points into a plot of the resulting color visual field.

18. The system of claim 13, wherein the stimuli target decreases in size as it moves along the individual paths toward the fixation structure to give the patient the perception that the stimuli target is the same distance from the eye at all times.

19. The system of claim 13, including a plurality of predetermined substantially linear paths, extending in directions radially outward from the fixation structure toward the viewing area perimeter, wherein the plurality of predetermined paths are spaced apart by substantially equal angles of separation, and wherein each quadrant of the viewing area includes at least two predetermined paths therein.

20. The system of claim 19, including a stimuli target configured to continuously and automatically move along the predetermined paths in a direction beginning at a beginning point on the viewing area and continuing toward an ending point for each path, wherein the stimuli target completes movement on a first path before beginning movement on a second path.

21. The system of claim 13, wherein the fixation structure has a central focal target and an orbiting focal symbol to hold the attention of the patient.

* * * * *

UNITED STATES PATENT AND TRADEMARK OFFICE
CERTIFICATE OF CORRECTION

PATENT NO. : 5,883,692
DATED : March 16, 1999
INVENTOR(S) : Dale Lawrence Agonis, et al.

It is certified that error appears in the above-identified patent and that said Letters Patent is hereby corrected as shown below:

<u>Column 6,</u>
Line 58, delete "of" and insert therefor -- or --

<u>Column 7,</u>
Line 21, delete "patent" and insert therefor -- patient --

<u>Column 8,</u>
Line 40, delete "form" and insert therefor -- from --

<u>Column 9,</u>
Line 8, delete "and" and insert therefor -- an --
Line 34, delete "minimun" and insert therefor -- minimum --

<u>Column 10,</u>
Line 67, delete "he"" and insert therefor -- the --

<u>Column 11,</u>
Line 3, delete "wary" and insert therefor -- wavy --
Line 24, delete "boudaries" and insert therefor -- boundaries --

Signed and Sealed this

Ninth Day of October, 2001

*Attest:*

NICHOLAS P. GODICI
*Attesting Officer*     *Acting Director of the United States Patent and Trademark Office*